(12) United States Patent
Carter et al.

(10) Patent No.: US 8,512,966 B2
(45) Date of Patent: Aug. 20, 2013

(54) METHOD FOR SENSING A CHEMICAL

(75) Inventors: Timothy Joseph Nicholas Carter, Sittingbourne (GB); Steven Andrew Ross, Sittingbourne (GB)

(73) Assignee: Vivacta Ltd., Sittingbourne, Kent (GB)

( * ) Notice: Subject to any disclaimer, the term of this patent is extended or adjusted under 35 U.S.C. 154(b) by 428 days.

(21) Appl. No.: 12/935,326

(22) PCT Filed: Mar. 31, 2009

(86) PCT No.: PCT/GB2009/050312
§ 371 (c)(1),
(2), (4) Date: Dec. 22, 2010

(87) PCT Pub. No.: WO2009/122208
PCT Pub. Date: Oct. 8, 2009

(65) Prior Publication Data
US 2011/0104708 A1    May 5, 2011

(30) Foreign Application Priority Data

Apr. 2, 2008 (GB) .................................. 0805954.5
Sep. 16, 2008 (GB) .................................. 0816930.2

(51) Int. Cl.
*G01N 31/00* (2006.01)
*G01N 33/53* (2006.01)

(52) U.S. Cl.
USPC ........... 435/7.21; 435/7.1; 436/501; 436/518; 424/130.1; 424/9.1; 530/300; 530/350

(58) Field of Classification Search
None
See application file for complete search history.

(56) References Cited

FOREIGN PATENT DOCUMENTS
WO        2004090512 A        10/2004

*Primary Examiner* — Lisa Cook
(74) *Attorney, Agent, or Firm* — Rothwell, Figg, Ernst & Manbeck, P.C.

(57) ABSTRACT

The present invention relates to a method for detecting an analyte (10) in a sample, comprising the steps of: providing a transducer comprising a pyroelectric or piezoelectric element and electrodes which is capable of transducing a change in energy to an electrical signal, a first reagent immobilised on the transducer, and a second reagent (11) releasably bound to the first reagent and having a label attached thereto which is capable of absorbing electromagnetic radiation to generate energy by non-radiative decay, wherein either the first or second reagent has a binding site which allows binding to the other and which is capable of preferentially binding to the analyte or a derivative of the analyte; exposing the transducer to the sample thereby allowing the analyte or a derivative of the analyte to bind to the binding site and displace the second reagent; irradiating the sample with electromagnetic radiation; transducing the energy generated into an electrical signal; and detecting the electrical signal. The invention also provides a device for carrying out the method.

27 Claims, 9 Drawing Sheets

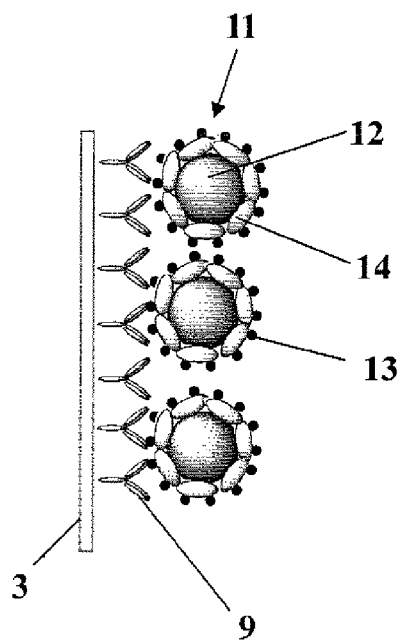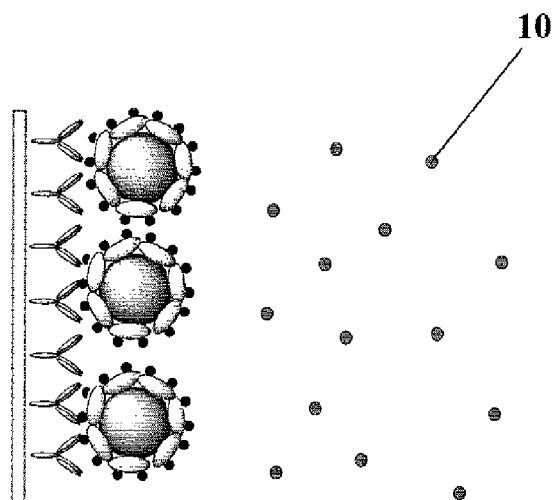
Fig. 2a  Fig. 2b
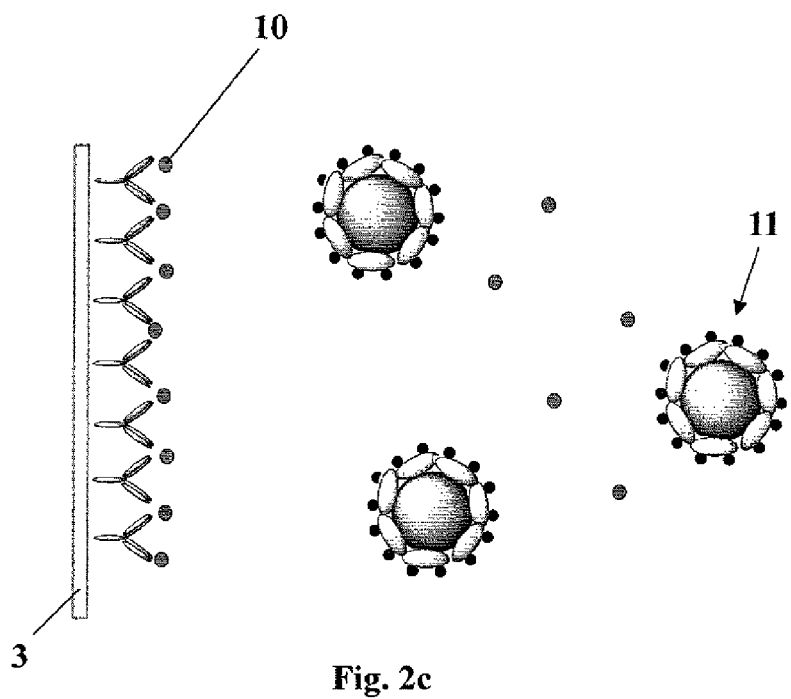
Fig. 2c

METHOD FOR SENSING A CHEMICAL

The present invention relates to a method for sensing a chemical, and in particular to an immunoassay employing a chemical sensing device containing a piezo/pyroelectric transducer.

An immunoassay is a test which measures the presence, or more usually the concentration, of an analyte in a biological fluid. It typically involves the specific binding of an antigen to an antibody. The antibody can be polyclonal or monoclonal, monoclonal antibodies having several benefits, including reproducibility of manufacture and containment of binding to one epitope of an analyte. In order to provide a quantifiable measure of the concentration of the analyte, the response is compared to standard samples of known concentration. The concentration of the antibody or antigen may be determined by a variety of methods, although one of the most common is to label either the antigen or antibody and detect the presence of the label.

Immunoassays can be competitive or non-competitive. In a competitive immunoassay, the antigen in the unknown sample competes with labelled antigen (reporter) to bind to the antibodies present. The amount of labelled antigen bound to the antibody site is then measured. Clearly the response will be inversely proportional to the concentration of antigen in the unknown sample. In a non-competitive immunoassay, also referred to as an immunometric assay, the antigen in the unknown sample binds to a capture antibody in the presence of an excess of labelled antibodies, thus fowling a "sandwich" and the amount of bound antigen in this "sandwich" is measured. Unlike the competitive method, the results of the non-competitive method will be directly proportional to the concentration of the antigen.

In a typical competitive immunoassay, an antibody specific for an antigen of interest is immobilised (i.e. attached to) a polymeric support such as a sheet of polystyrene. A drop of the sample to be tested, e.g. a cell extract or a sample of serum or urine, is laid on the sheet. In addition, a known amount of reporter (i.e. labelled) antigen is also added to the sample. The labelled and unlabelled antigen then compete for binding to the antibodies immobilised on the polymeric support. The polymeric support is washed after formation of the antibody-antigen complexes. The concentration of the reporter antigen bound to the sheet is determined. The signal from the reporter antigen is then inversely proportional to the quantity of antigen in the sample. This assay and other variations on this type of assay are well known, see, for example, "The Immunoassay Handbook, 2nd Ed." David Wild, Ed., Nature Publishing Group, 2001.

A variation on this immunoassay is the so-called "displacement immunoassay". In this assay, the reporter antigen is pre-attached to the antibodies present on the polymeric support. The unknown antigen is then added to the system and the antigen displaces the reporter antigen from the surface of the support. The loss of the reporter antigen is determined and equated with the concentration of the unknown antigen in the sample. However, the measurement of the displacement of the reporter antigen is far from straight forward.

For example, Giese at al (U.S. Pat. No. 4,801,726) describe a similar procedure. In a so-called "hit-and-run" immunoassay, a fluorescently-labelled antibody pre-bound to an immobilised-antigen column is displaced when an aliquot of a sample is added to the aqueous stream passing over the column. If the aliquot contains the analyte, a small fraction of the reporter antibody is displaced and measured fluorimetrically in the downstream effluent. This is designed as a "repetitive" immunoassay, reusing the same column many times. This concept has been developed for the continuous screening and very intermittent detection of explosives. Ligler et al (U.S. Pat. No. 5,183,740) describe a very similar fluorimetric column-based system for TNT. This is further developed into a membrane-based system by the same group (U.S. Pat. No. 6,750,031 and Rabbany et al. Biosensors & Bioelectronics 1998, 13, 939-944). In all these cases the immuno-displacement occurs in the column or membrane and the detection occurs in a downstream instrument.

Herron et al (U.S. Pat. No. 6,979,567) describe the use of a total internal reflection fluorescent detector in competitive immunoassay, including monitoring the displacement of an analyte from a saturated surface. V. I. Chegel et al. Sensors Actuators B 1998, 48, 456-460 and P. T. Charles et al. Anal. Chim. Acta 2004, 525, 199-204 describe displacement assays using fluorescence/chemiluminescence methods for detecting the reporter species.

However, there remains a need in the art for a more straight forward detection methodology.

Accordingly, the present invention provides a method for detecting an analyte in a sample, comprising the steps of:

providing a transducer comprising a pyroelectric or piezoelectric element and electrodes which is capable of transducing a change in energy to an electrical signal, a first reagent immobilised on the transducer, and a second reagent releasably bound to the first reagent and having a label attached thereto which is capable of absorbing electromagnetic radiation to generate energy by non-radiative decay, wherein either the first reagent or the second reagent has a binding site which allows binding to the other and which is capable of preferentially binding to the analyte or a derivative of the analyte;

exposing the transducer to the sample thereby allowing the analyte or a derivative of the analyte to bind to the binding site and displace the second reagent;

irradiating the sample with electromagnetic radiation;

transducing the energy generated into an electrical signal; and detecting the electrical signal.

The present invention also provides a device for detecting an analyte in a sample comprising:

a transducer having a pyroelectric or piezoelectric element and electrodes which is capable of transducing a change in energy to an electrical signal;

a first reagent immobilised on the transducer;

a second reagent releasably bound to the first reagent and having a label attached thereto which is capable of absorbing electromagnetic radiation to generate energy by non-radiative decay, wherein either the first reagent or the second reagent has a binding site which allows binding to the other and which is capable of preferentially binding to the analyte or a derivative of the analyte;

a source of electromagnetic radiation; and a detector for detecting the electrical signal.

The present invention further provides the use of a transducer having a pyroelectric or piezoelectric element and electrodes for monitoring a labelled reagent in a displacement immunoassay.

The present invention will now be described with reference to the drawings, in which.

Figure 1:
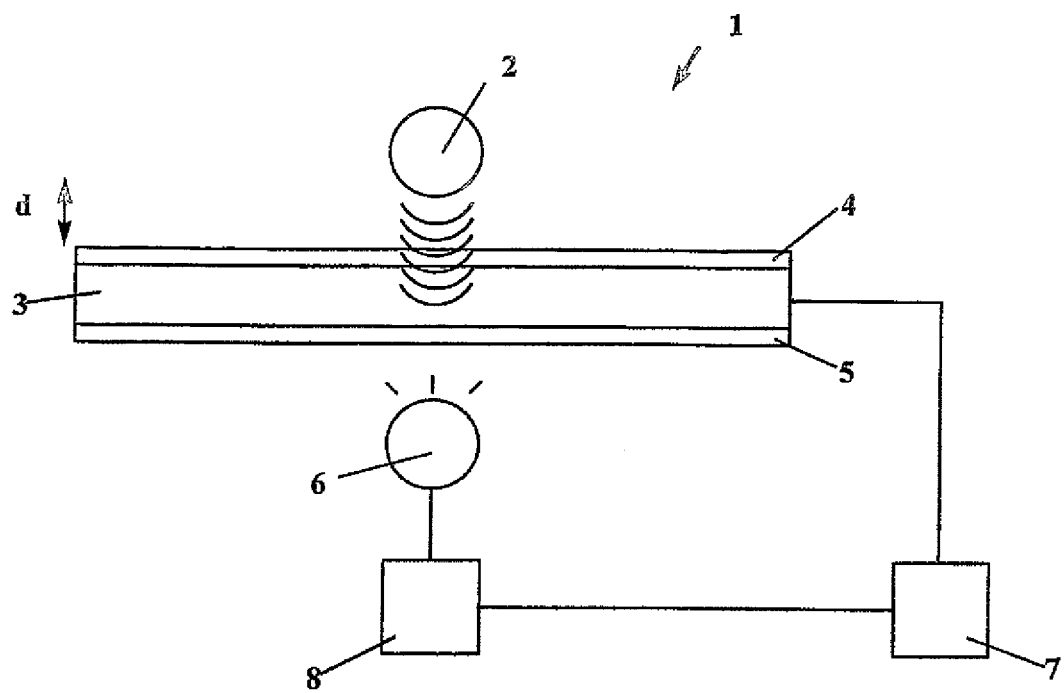
FIG. 1 shows a device according to WO 2004/090512.

The method of the present invention provides for the detection of an analyte in a sample. As a first step, the method includes the provision of a transducer having a pyroelectric or piezoelectric element and electrodes which is capable of transducing a change in energy to an electrical signal and exposing the sample to the transducer. Such transducers are known in the art, see for example WO 90/13017 and WO 2004/090512. In this regard, FIG. 1 shows the principle of the chemical sensing device 1 suitable for use in the present invention. The device 1 relies on heat generation in a substance 2 on irradiation of the substance 2 with electromagnetic radiation. The device 1 comprises a pyroelectric or piezoelectric transducer 3 having electrode coatings 4,5. The transducer 3 is preferably a poled polyvinylidene fluoride film. The electrode coatings 4,5 are preferably formed from indium tin oxide having a thickness of about 35 nm, although almost any thickness is possible from a lower limit of 1 nm below which the electrical conductivity is too low and an upper limit of 100 nm above which the optical transmission is too low (it should not be less than 95% T). A substance 2 is held on or proximal to the transducer 3 using any suitable technique, shown here immobilised on the upper electrode coating 4. The reagent may be in any suitable form and a plurality of reagents may be deposited. Preferably, the substance 2 is adsorbed on to the upper electrode, e.g. covalently coupled or bound via intermolecular forces such as ionic bonds, hydrogen bonding or van der Waal's forces. A key feature of this device is that the substance 2 generates heat when irradiated by a source of electromagnetic radiation 6, such as light, preferably visible light. The light source may be, for example, an LED. The light source 6 illuminates the substance 2 with light of the appropriate wavelength (e.g. a complementary colour). Although not wishing to be bound by theory, it is believed that the substance 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. The device of the present invention is calibrated for the particular reagent being measured and hence the precise form of the energy generated by the non-radiative decay does not need to be determined. Unless otherwise specified the term "heat" is used herein to mean the energy generated by non-radiative decay. The light source 6 is positioned so as to illuminate the substance 2. Preferably, the light source 6 is positioned substantially perpendicular to the transducer 3 and electrodes 4,5 and the substance 2 is illuminated through the transducer 3 and electrodes 4,5. The light source may be an internal light source within the transducer in which the light source is a guided wave system. The wave guide may be the transducer itself or the wave guide may be an additional layer immobilised on the transducer. Preferably a wavelength of 525 nm is used, although other suitable wavelengths may be used with advantageous properties described, for example, in WO 2007/107716.

The energy generated by the substance 2 is detected by the transducer 3 and converted into an electrical signal. The electrical signal is detected by a detector 7. The light source 6 and the detector 7 are both under the control of the controller 8.

In one embodiment, the light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 2-50 Hz, more preferably 5-15 Hz and most preferably 10 Hz. This corresponds to a time delay between pulses of 20-500 ms, 66-200 ms and 100 ms, respectively. In addition, the so-called "mark-space" ratio, i.e. the ratio of on signal to off signal is preferably one although other ratios may be used without deleterious effect. Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. The applicant has found that this time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

Thus substance 2 may be separated from the transducer surface and a signal may still be detected. Moreover, not only is the signal detectable through an intervening medium capable of transmitting energy to the transducer 3, but different distances, d, may be distinguished (this has been termed "depth profiling") and that the intensity of the signal received is proportional to the concentration of the substance 2 at the particular distance, d, from the surface of the transducer 3.

FIG. 2 shows the device I from FIG. 1 in a displacement immunoassay in accordance with the present invention. In this embodiment, the first reagent is an antibody and the second reagent is a labelled analyte. The transducer 3 is shown in a vertical arrangement in FIG. 2a. The advantages of this arrangement are discussed in more detail hereinbelow. The transducer 3 is coated with a first reagent shown in FIG. 2 as an antibody 9 (an immobilised capture antibody). The antibody 9 has been raised against the analyte 10 (see FIG. 2b) and selectively binds to the analyte 10 when the sample is introduced. The transducer also has a labelled analyte 11 (which corresponds to the substance 2 in FIG. 1). The labelled analyte 11 includes a label 12 having a plurality of analyte moieties 13 attached thereto, optionally via a linker 14. The antibody 9 is pre-incubated with an excess of the labelled analyte 11. The transducer 3 having a layer of the antibodies 9 is then typically covered with a preservative layer (not shown) and dried. In this state, the transducer may be stored for extended periods of time.

Figure 2D:
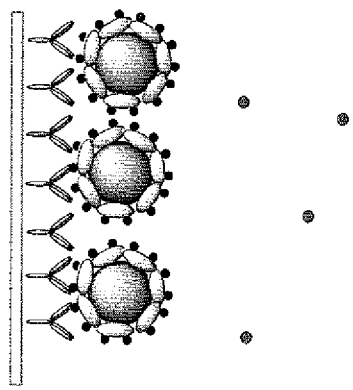
FIGS. 2 to 4 show schematic representations of the method of the present invention.
Figure 2E:
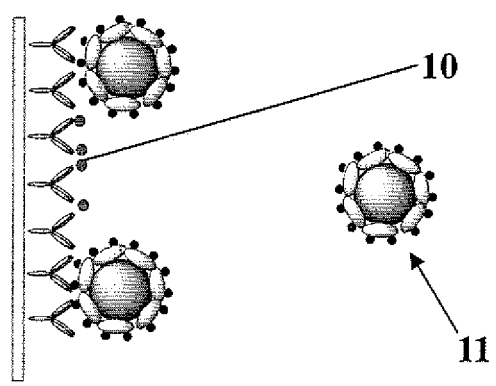

In use, as shown in FIG. 2b, the transducer is exposed to the sample containing an unknown concentration of the analyte 10. The analyte 10 diffuses rapidly to the transducer surface and displaces the labelled analyte 11 from the antibodies 9, see FIG. 2c. The displacement will usually occur because the analyte has a higher binding constant than the labelled analyte (second reagent), i.e. because it has faster "on" rate of reaction compared with the "on" rate of the labelled analyte (second reagent), or a slower "off" rate of reaction compared with the "off" rate of the labelled analyte or both. The reaction can be monitored in real time using the transducer 3 in the manner explained hereinabove with reference to FIG. 1. Since the assay may be performed without any reagents other than those presented on the transducer surface at the start of the assay, the assay may be termed "reagentless". Preferably the first and second reagents are the sole reagents present. The assay shown in FIG. 2c is a schematic representation of the displacement of the labelled analyte in the presence of a high concentration of analyte in the sample. FIGS. 2d and 2e, respectively, show displacement at low concentrations of analyte. This leads to fewer labelled analytes 11 being released from the surface of the transducer 3. The second reagent released from the surface is free to diffuse away from the surface. Although the removal of the second reagent from the surface may be facilitated, for example under the force of gravity/buoyancy, preferably the second reagent is allowed to become separated from the surface solely by diffusion.

Figure 3A:
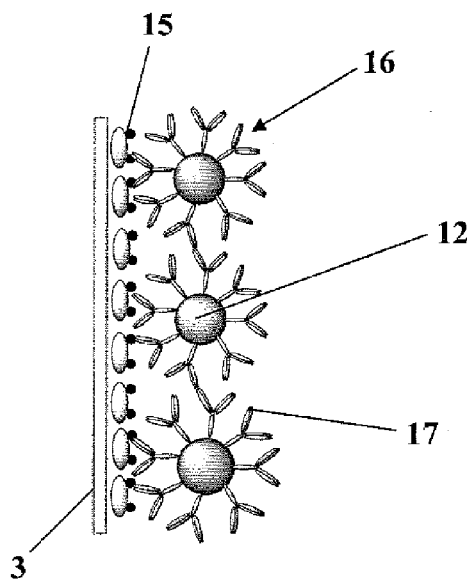

The method of the present invention permits detection of the binding of the analyte 10 (albeit indirectly by monitoring the displacement of the labelled analyte 11) in real time, without separation and washing steps. This is a significant advantage in the art. Thus, in a preferred embodiment, the assay is carried out without removing the sample from the transducer 3 at any time during the assay. Moreover, no further intervention (e.g. to separate bound and unbound second reagent) is required between exposing the transducer to the sample and irradiating the sample FIG. 3 shows an embodiment where first reagent is an immobilised analyte and the second reagent is a labelled antibody. The transducer 3 is shown in a vertical arrangement in FIG. 3a. The first reagent in FIG. 3a is an immobilised analyte 15. The second reagent is labelled antibody 16 (a reporter antibody), which corresponds to the substance 2 in FIG. 1. The labelled antibody 16 includes a label 12 having a plurality of antibodies 17 attached thereto. The antibody 17 has been raised against the analyte 10 and selectively binds to the analyte when the sample is introduced.

Figure 3B:
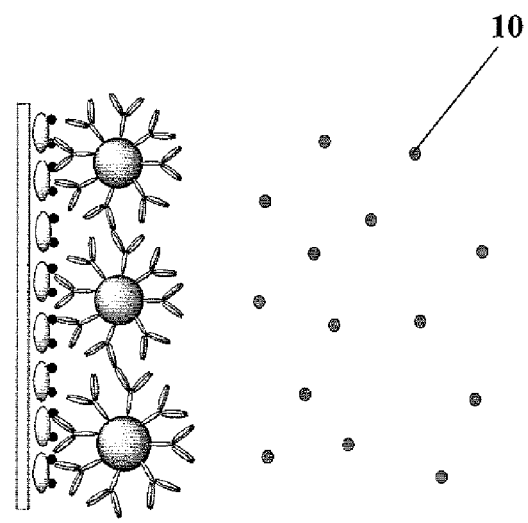
Figure 3C:
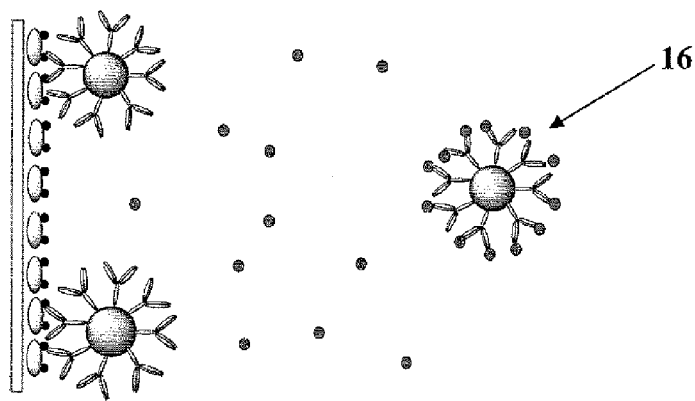

In use, as shown in FIG. 3b, the transducer is exposed to the sample containing an unknown concentration of the analyte 10. The analyte 10 diffuses rapidly to the transducer surface and, because of its higher binding constant or faster "on" rate of reaction compared with the "off" rate of the second reagent, displaces the immobilised analyte 15 from the antibodies 17, see FIG. 3c. The reaction can be monitored in real time using the transducer 3 in the manner explained hereinabove with reference to FIG. 1.

It has been shown with reference to FIGS. 2 and 3 that prior to the addition of the sample, the first reagent immobilised on the transducer and the second reagent are releasably bound to one another. The binding will typically be through non-covalent intermolecular forces, e.g. the binding between an antibody and antigen or between complementary nucleic acids. The binding is releasable in that the binding may be disrupted by the analyte or derivative thereof leading to displacement of the second reagent from the first reagent. The binding site which allows binding of the first reagent to the second reagent may be present on the first reagent, the second reagent or on both reagents, and is capable of preferentially binding to the analyte or a derivative of the analyte. The binding is preferential in that the presence of the analyte leads to disruption of the binding between the first reagent and the second reagent and the reagent which has the binding site for the analyte or derivative thereof becomes bound to the analyte or derivative thereof.

Although the relevant reagents are exemplified in FIGS. 2 and 3 by antibodies, i.e. an immobilised capture antibody (FIG. 2) or a reporter antibody (FIG. 3), the present invention is not limited thereto. Thus, although the first reagent in FIG. 2 and the second reagent in FIG. 3 are preferably antibodies, other reagents may also be used, such as nucleic acids. In a preferred embodiment, the present invention provides a method of performing a (displacement) immunoassay to detect an analyte (hapten) in a sample, comprising the steps of: providing a transducer comprising a pyroelectric or piezoelectric element and electrodes which is capable of transducing a change in energy to an electrical signal, a capture antibody immobilised on the transducer, and a labelled analyte bound to the capture antibody having a label attached thereto which is capable of absorbing electromagnetic radiation to generate energy by non-radiative decay; exposing the transducer to the sample thereby allowing the analyte or a derivative of the analyte to bind to the immobilised capture antibody and displace the labelled analyte from the transducer; irradiating the sample with electromagnetic radiation; transducing the energy generated into an electrical signal; and detecting the electrical signal. Alternatively, comprising the steps of: providing a transducer comprising a pyroelectric or piezoelectric element and electrodes which is capable of transducing a change in energy to an electrical signal, an analyte immobilised on the transducer, and a labelled antibody bound to the immobilised analyte having a label attached thereto which is capable of absorbing electromagnetic radiation to generate energy by non-radiative decay; exposing the transducer to the sample thereby allowing the analyte or a derivative of the analyte to bind to the labelled antibody and displace the labelled antibody from the transducer; irradiating the sample with electromagnetic radiation; transducing the energy generated into an electrical signal; and detecting the electrical signal.

The first reagent 9,15 is shown in FIGS. 2 and 3 immobilised on the surface of the transducer 3 and is preferably adsorbed on to the transducer. The surface may also be covered by further coatings to stabilise the surface, e.g. Stabilcoat from SurModics Inc, Eden Prairie, Minn., USA.

As discussed with reference to FIGS. 2 and 3, the label 12 is capable of absorbing the electromagnetic radiation generated by the radiation source to generate energy by non-radiative decay. Thus, to detect the presence of the label 12 proximal to the transducer 3, the sample is irradiated with a series of pulses of electromagnetic radiation. The transducer 3 transduces the energy generated into an electrical signal and the electrical signal is detected by detector 7.

The label 12 may be any material which is capable of interacting with the electromagnetic radiation generated by the radiation source to generate energy by non-radiative decay. Preferably the label is selected from, but not limited to, a carbon particle, a coloured-polymer particle (e.g. coloured latex), a dye molecule, an enzyme, a fluorescent molecule, a metal (e.g. gold) particle, a haemoglobin molecule, a magnetic particle, a nanoparticle having a non-conducting core material and at least one metal shell layer, a red blood cell, and combinations thereof.

In the case of a magnetic particle, the electromagnetic radiation is radio frequency radiation. All of the other labels mentioned hereinabove employ light, which can include IR or UV radiation. Gold particles are commercially available or may be prepared using known methods (see for example G. Frens, Nature, 241, 20-22 (1973)). For a more detailed explanation of the nanoparticle label see U.S. Pat. No. 6,344,272 and WO 2007/141581.

In one embodiment (diffusion controlled), the present invention uses a particle having a particle size of 20 to 1,000 nm, more preferably 100 to 500 nm. By particle size is meant the diameter of the particle at its widest point. Preferably, the particle has a density of 0.5 to 3.0 g/mL, more preferably 1.5-2.0 g/mL and most preferably 1.8 g/mL. In a particularly preferred embodiment, the particle is a carbon particle having the afore-mentioned particle size and density, although other materials could be used, such as polystyrene or latex.

In another embodiment (gravity assisted), the present invention uses a particle having a particle size of 20 to 1,000 nm, more preferably 100 to 500 nm. Preferably, the particle has a density of 1.5 to 23 g/mL, more preferably 15-20 g/mL and most preferably 19 g/mL. In a particularly preferred embodiment, the particle is a gold particle having the afore-mentioned particle size and density, although other dense materials could be used, such as osmium or iridium.

The label 12 is proximal to the transducer when the binding event has occurred. That is the label is sufficiently close to the surface of the transducer for the transducer to be able to detect the energy generated by the label on irradiation of the sample. The actual distance between the label and the surface of the transducer will, however, depend on a number of variables, such as the size and nature of the label, the size and nature of the antibodies and the analyte, the nature of the sample medium, and the nature of the electromagnetic radiation and the corresponding settings of the detector. With regard to the nature of the electromagnetic radiation, the device of the present invention may include a radiation source which is adapted to generate a series of pulses of electromagnetic radiation and the detector is adapted to determine the time delay between each pulse of electromagnetic radiation from the radiation source and the generation of the electric signal thereby allowing a precise determination of the position of the label with respect to the transducer as discussed with reference to FIG. 1.

The unknown sample is expected to contain the analyte, but of course the assay of the present invention may be used to determine the presence or absence of the analyte. The analyte is preferably a small molecule insofar as the assay is ideally suited for such a molecule, although the present invention is not limited thereto. The term "small molecule" used herein is a term of the art and is used to distinguish the molecule from macromolecules such as proteins and nucleic acids. A small molecule is often referred to in the field of immunoassays as a "hapten", being a small molecule which, when attached to a large carrier molecule such as a protein, can elicit an immune response and includes molecules such as hormones and synthetic drugs. A small molecule of this type will typically have a molecular weight of 2,000 or less, often 1,000 or less and even 500 or less. The first reagent may be adapted to bind to the analyte itself, although the analyte can undergo a chemical reaction or initial complexing event before binding to the first reagent. For example, the analyte might be protonated/deprotonated in the pH of the assay conditions. Thus, the analyte which is bound to the first reagent may be analyte itself or a derivative of the analyte; both are included within the scope of the present invention.

The sample which may or may not contain the analyte of interest will generally be a fluid sample and usually a biological sample, such as a bodily fluid, e.g. blood, plasma, saliva, serum or urine. The sample may contain suspended particles and may even be whole blood. An advantage of the method of the present invention is that the assay may be performed on a sample which does contain suspended particles without unduly influencing the results of the assay. The sample will typically be in the order of microlitres (e.g. 1-100 µL, preferably 1-10 µL). In order to hold a fluid sample, the transducer is preferably located in a sample chamber having two side walls, an upper surface and a lower surface and more preferably a well. In a preferred embodiment, the transducer is integral with the chamber, i.e. it forms one of the side walls, or upper or lower surface which define the chamber. Clearly, the reagent 9 and the labelled analyte 11 will be on the interior surfaces of the chamber to allow contact with the sample. The sample may simply be retained by surface tension forces, for example, inside a capillary channel.

In an embodiment of the present invention, gravity may be used to assist in the displacement of the labelled analyte 11 from the surface of the transducer. That is, the transducer forms the upper surface of the chamber and the labelled analyte is more dense than the medium of the sample, or the transducer forms the lower surface of the chamber and the label is less dense than the medium of the sample. Where the labelled analyte is more dense than the liquid medium of the sample the labelled analyte settles towards the lower surface (the base) of the sample chamber under the influence of gravity. Alternatively, the labelled analyte may be less dense than the liquid medium of the sample so that the labelled analyte floats towards the upper surface of the sample chamber (the lid) under the force of buoyancy. In other words, the displacement of the labelled analyte is assisted by sedimentation or by floatation under the force of gravity/buoyancy. This is shown in greater detail with reference to FIG. 4.

Figure 4A:
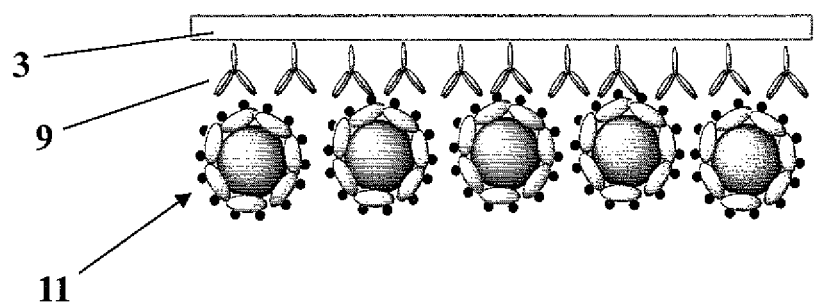
Figure 4B:
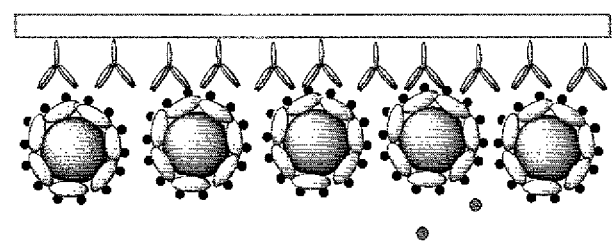
Figure 4C:
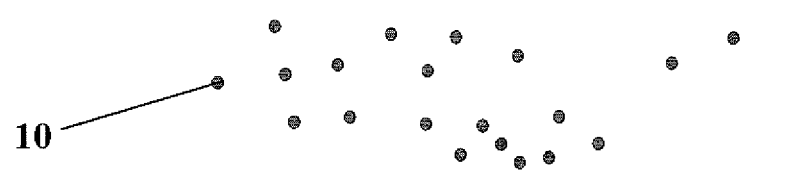
Figure 4D:
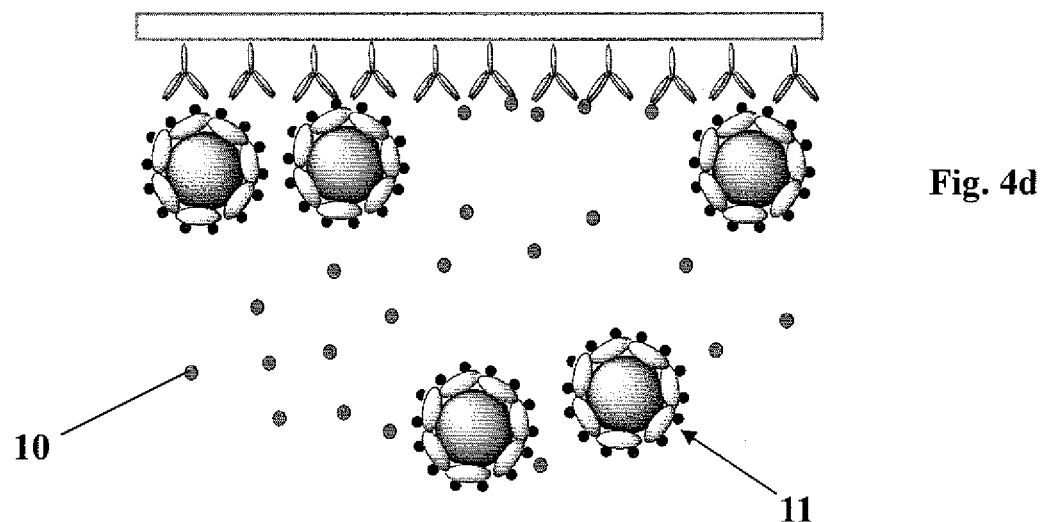
Figure 4E:
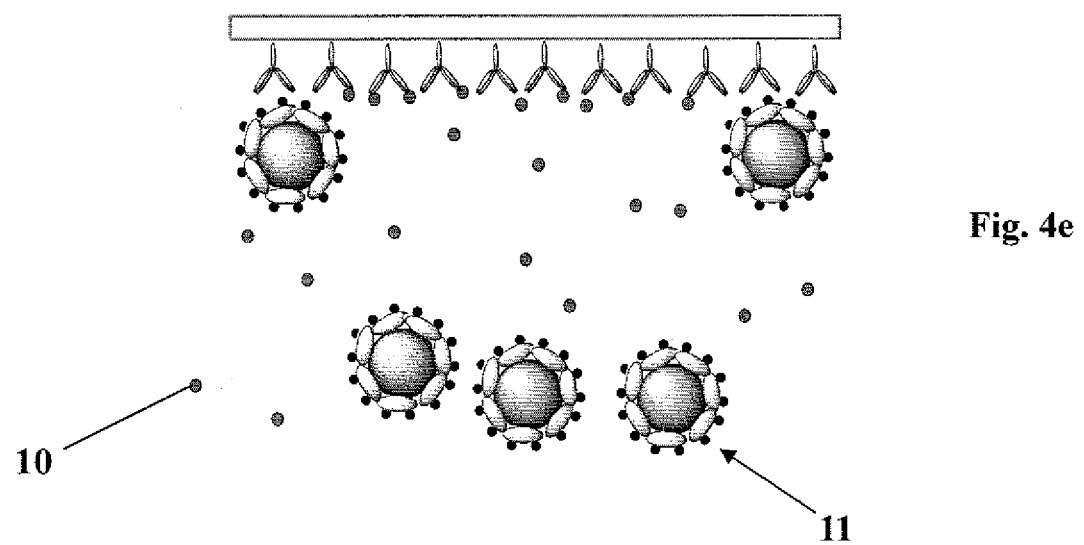

FIG. 4a-4e shows the assay of the present invention where the transducer forms the upper surface of the sample chamber. In FIG. 4a, the transducer 3 contains a layer of the immobilised antibody 9 and a layer of the labelled analyte 11. The sample is added, as shown in FIG. 4b, and the analyte 10 diffuses towards the transducer. The displacement of the labelled analyte 11 is shown schematically for low, intermediate and high analyte concentrations in FIGS. 4c-4e. The labelled analyte has a greater density than the sample medium and hence tends to settle under the influence of gravity.

The present invention also provides a device for performing the assay described herein. In a preferred embodiment, the device consists essentially of the above-described features. By "essentially" is meant that no other features are required to perform the assay. The device may take the form of a hand-held portable reader and a disposable device containing the transducer. The sample is collected in an essentially closed system, mixed with the second reagent and placed in a reader that would perform the irradiation of the sample and detection of the resultant electrical signal. The present invention further provides for the use of a transducer having a pyroelectric or piezoelectric element and electrodes for monitoring a labelled reagent in a displacement immunoassay as described herein.

EXAMPLES

Example 1

Preparation of Active Piezo/Pyrofilm Biosensors

A poled piezoelectric polyvinylidene fluoride (PVDF) bimorph film, coated in indium tin oxide used as the sensing device in the following example, was dip-coated in polystyrene solution (1% in toluene) in a low humidity environment to give a polystyrene layer on top of the indium tin oxide. This was then coated in polystreptavidin solution (200 µg/mL in PBS—10 mmol/L phosphate buffer, pH 7.5, containing 2.7 mmol/L KCl, 137 mmol/L NaCl and 0.05% Tween) by incubation at room temperature overnight. Polystreptavidin was prepared as described by Tischer et al (U.S. Pat. No. 5,061,640).

To prepare a "capture" surface the polystreptavidin surface was incubated with either biotinylated anti-testosterone, giving an antibody coated surface (C1), or with biotinylated testosterone giving an antigen coated surface (C2). For C1, 10

μg/mL of biotinylated anti-testosterone (HyTest Ltd, Turku, Finland, Cat #2T2-biotin, or Accurate Chemical Co, Westbury, N.Y., USA, Cat #BHS113) in PBS was incubated at room temperature overnight and then washed with excess PBS and coated with Stabilcoat (SurModics Inc, Eden Prairie, Minn., USA) before drying at 40° C. For C2, 30 nmol/L of 7α-C6-biotinylated testosterone, prepared as described in Luppa et al. Clin. Chem. 1997, 43, 2345, in PBS was incubated at room temperature overnight and then washed with excess PBS and coated with Stabilcoat (SurModics Inc, Eden Prairie, Minn., USA) before drying at 40° C.

Example 2

Preparation of Carbon-Labelled Reporter Conjugates

Carbon-labelled reporter conjugates were prepared essentially as described by Van Doorn et al. (U.S. Pat. No. 5,641,689). To prepare antibody coated reporter conjugates (R1), 1 mL of Special Black-4 RCC nominally 150 nm carbon particles (Degussa, Essen, Germany) in 5 mmol/L phosphate buffer, pH 6.2 was incubated with 200 μg/mL polystreptavidin solution overnight at room temperature with shaking, resulting in a streptavidin-coated surface (A1). The resultant carbon conjugate was washed (by centrifugation, pelleting and resuspension) 10 μg/mL of biotinylated anti-testosterone (HyTest Ltd, Turku, Finland, Cat #2T2-biotin, or Accurate Chemical Co, Westbury, N.Y., USA, Cat #BHS 113) in PBS was then incubated overnight with 1 mL of this streptavidin-coated carbon particle suspension with shaking. The resultant carbon conjugate was washed (by centrifugation, pelleting and resuspension) three times with 0.05 mol/L borate buffer at pH 8.5 and stored in this buffer in the dark at 4° C. To prepare the antigen coated reporter (R2), 1 mL of streptavidin-coated carbon particles (A1) in 5 mmol/L phosphate buffer, pH 6.2 was incubated with 30 mmol/L of 7α-C6-biotinylated testosterone, prepared as described in Luppa et al. Clin. Chem. 1997, 43, 2345, at room temperature overnight with shaking. The resultant carbon conjugate was washed three times with 0.05 mol/L borate buffer at pH 8.5 as above and stored in this buffer in the dark at 4° C.

Example 3

Preparation of Gold-Labelled Reporter Conjugates

Gold-labelled reporter conjugates were prepared essentially as described by Frens G. Nature 1973, 241, 20-22 or Roth J. The colloidal gold marker system for light and electron microscopic cytochemistry. In Bullock G R, Petrusz P, eds. Techniques in Immunocytochemistry, Vol 2. New York, N.Y., Academic Press, 1983, 216-284. To prepare antibody coated reporter conjugates (R3), 1 mL of mono-dispersed nominally 150 nm gold particles (BBI International. Cardiff, UK) in 5 mmol/L phosphate buffer, pH 6.2 was incubated with 200 μg/mL streptavidin solution overnight at room temperature with shaking, resulting in a streptavidin-coated surface (A2). The resultant gold conjugate was washed (by centrifugation, pelleting and resuspension) 10 μg/mL of biotinylated anti-testosterone (HyTest Ltd, Turku, Finland, Cat #2T2-biotin, or Accurate Chemical Co, Westbury, N.Y., USA, Cat #BHS113) in PBS was then incubated overnight with 1 mL of this streptavidin-coated gold particle suspension with shaking. The resultant gold conjugate was washed (by centrifugation, pelleting and resuspension) three times with 0.05 mol/L borate buffer at pH 8.5 and stored in this buffer in the dark at 4° C. To prepare the antigen coated reporter (R4), 1 mL of streptavidin-coated gold particles (A2) in 5 mmol/L phosphate buffer, pH 6.2 was incubated with 30 nmol/L of 7α-C6-biotinylated testosterone, prepared as described in Luppa et al. Clin. Chem. 1997, 43, 2345, at room temperature overnight with shaking. The resultant gold conjugate was washed three times with 0.05 mol/L borate buffer at pH 8.5 as above and stored in this buffer in the dark at 4° C.

Example 4

Preparation of Reagent-Coated Antibody-Coated Film

To prepare a reagent-coated antibody-coated piezofilm surface, a piece of antibody-coated piezofilm (C1, described above) was incubated with either antigen-coated carbon (R2) or antigen-coated gold reagent (R4) (see above) in PBS at room temperature overnight and then washed with excess PBS and coated with Stabilcoat (SurModics Inc, Eden Prairie, Minn., USA) before drying at 40° C. to give carbon reagent coated (C3) or gold reagent coated (C4) reaction surfaces respectively.

Example 5

Preparation of Reagent-Coated Antigen-Coated Film

To prepare a reagent-coated antigen-coated piezofilm surface, a piece of antigen-coated piezofilm (C2, described above) was incubated with either antibody-coated carbon (R1) or antibody-coated gold reagent (R3) (see above) in PBS at room temperature overnight and then washed with excess PBS and coated with Stabilcoat (SurModics Inc, Eden Prairie, Minn., USA) before drying at 40° C. to give carbon reagent coated (C5) or gold reagent coated (C6) reaction surfaces respectively.

Example 6

Assay: Reagent-Coated Piezofilm Sensor, Carbon Label, Simple "Diffusion" Assay

Figure 5:
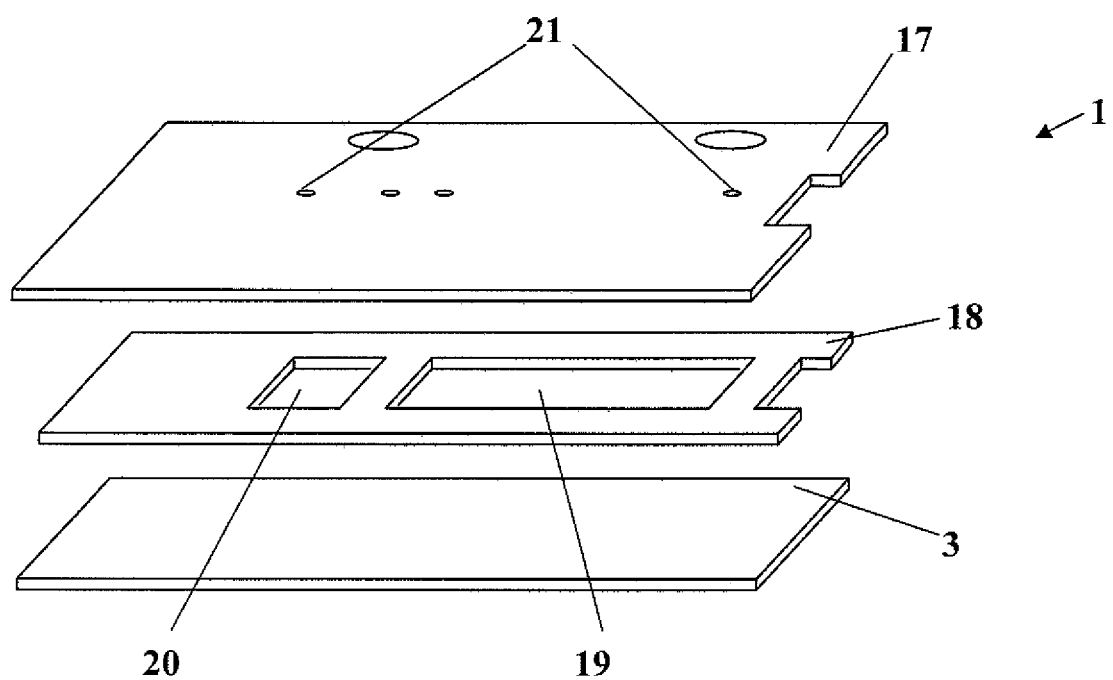
FIG. 5 shows a device according to the present invention.

As shown in FIG. 5, a sensor 1 was fabricated to perform the assay. The sensor 1 is fabricated from a piece of antibody-coated piezofilm 3 (C3 or C5, described above) and a piece of transparent polycarbonate lidding film 14. The films are spaced at a distance of approximately 500 microns using a spacer 18 piece of pressure sensitive adhesive-coated polyester film die-cut to form two unequally sized chambers 19,20; one chamber of approximate dimensions 30×10×0.5 mm for the assay reaction and a second smaller chamber 20 of dimensions 10×10×0.5 mm for a control reaction. Provision is made to allow for electrical connections to the top and bottom surfaces of the piezofilm in order to detect the charge generated.

Figure 6:
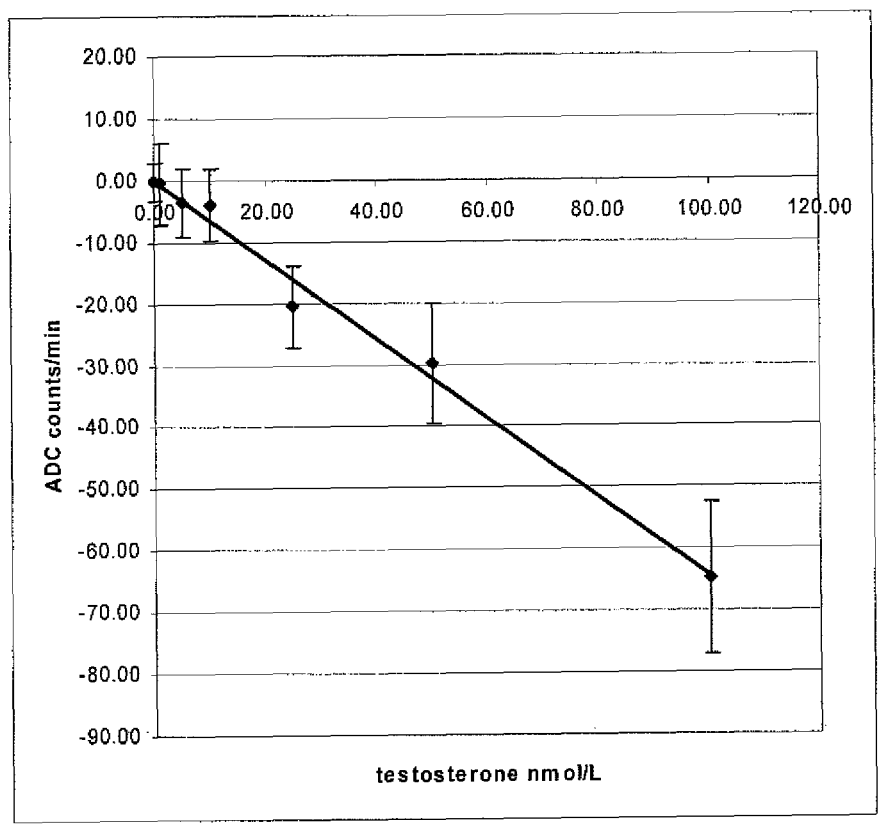
FIGS. 6 and 7 show graphs of counts against time for two assays, using the method of the present invention.

Assays are carried out by filling the larger chamber 19 (through a fill hole 21) with testosterone standards in PBS to give a final concentration range of 0.1-100 nmol/L. The control chamber 20 is simultaneously filled with an identical reaction mix to that in the assay chamber with the testosterone standard replaced with PBS. The entry and exit holes are sealed and the chamber assembly is connected to a test instrument such that the piezofilm is oriented vertically on the side face of the chamber. The piezofilm is then illuminated with chopped LED light sequentially with four LEDs (of wavelength 625 nm), of which three illuminate different areas of the surface of the assay chamber and one illuminates the piezofilm surface of the control chamber. For each LED pulse, a voltage is measured across the piezofilm using a lock-in amplifier and analogue to digital (ADC) converter. The ADC signal is plotted over time and the relationship of ADC counts/min against testosterone concentration is shown in FIG. 6. The data have been zeroed from the start point of the reaction so that only changes in signal are illustrated.

Example 7

Figure 7:
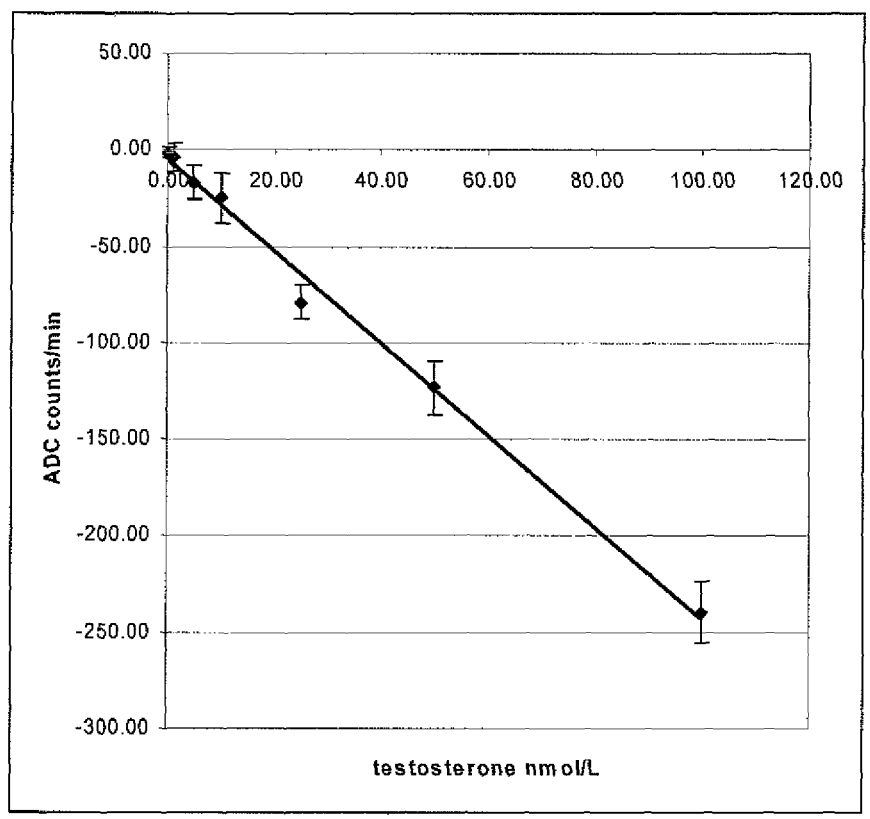

Assay: Reagent-Coated Piezofilm Sensor, Gold Label, "Gravity-Assisted Diffusion" Assay To perform the assay, a sample chamber is fabricated as set out in Example 6 (C4 or C6, described above). The assay is set up in the same manner as Example 6, except that the piezofilm is oriented horizontally with the piezofilm on the upper face of the chamber. The piezofilm is then illuminated with chopped LED light sequentially with 4 LEDs (of wavelength suitable for detecting larger gold labels, nominally 625 nm, see WO 2007/107716), of which three illuminate different areas of the surface of the assay chamber and one illuminates the piezofilm surface of the control chamber. For each LED pulse, a voltage is measured across the piezofilm using a lock-in amplifier and analogue to digital (ADC) converter. The ADC signal is plotted over time and the relationship of ADC counts/min against testosterone concentration is shown in FIG. 7. The data have been zeroed from the start point of the reaction, so that only changes in signal are illustrated.

The invention claimed is:

1. A method for detecting an analyte in a sample, comprising the steps of:
providing a transducer comprising a pyroelectric or piezoelectric element and electrodes which is capable of transducing a change in energy to an electrical signal, a first reagent immobilised on the transducer, and a second reagent releasably bound to the first reagent and having a label attached thereto which is capable of absorbing electromagnetic radiation to generate energy by non-radiative decay, wherein either the first or second reagent has a binding site which allows binding to the other and which is capable of preferentially binding to the analyte or a derivative of the analyte;
exposing the transducer to the sample thereby allowing the analyte or a derivative of the analyte to bind to the binding site and displace the second reagent;
irradiating the sample with electromagnetic radiation;
transducing the energy generated into an electrical signal; and
detecting the electrical signal.

2. A method as claimed in claim 1, wherein the transducer is located in a sample chamber having two side walls, an upper surface and a lower surface.

3. A method as claimed in claim 1, wherein the transducer forms one of the side walls of the chamber.

4. A method as claimed in claim 1, wherein the transducer forms the upper surface of the chamber and the second reagent is more dense than the medium of the sample.

5. A method as claimed in claim 1, wherein the transducer forms the lower surface of the chamber and the second reagent is less dense than the medium of the sample.

6. A method as claimed in claim 1, wherein the first reagent is an immobilised antibody and the second reagent is a labelled analyte.

7. A method as claimed in claim 1, wherein the first reagent is an immobilised analyte and the second reagent is a labelled antibody.

8. A method as claimed in claim 1, wherein the transducer further comprises a preservative coating over the transducer, first reagent and second reagent.

9. A method as claimed in claim 1, wherein the label is selected from a carbon particle, a coloured-polymer particle, a dye molecule, an enzyme, a fluorescent molecule, a metal, e.g. gold, particle, a haemoglobin molecule, a magnetic particle, a nanoparticle having a non-conducting core material and at least one metal shell layer, a red blood cell, and combinations thereof.

10. A method as claimed in claim 1, wherein the first reagent is adsorbed on to the transducer.

11. A method as claimed in claim 1, wherein the sample contains suspended particles.

12. A method as claimed in claim 11, wherein the sample is whole blood.

13. A method as claimed in claim 1, wherein the radiation source is adapted to generate a series of pulses of electromagnetic radiation and the detector is adapted to determine the time delay between each pulse of electromagnetic radiation from the radiation source and the generation of the electrical signal.

14. A method as claimed in claim 1, wherein the method is carried out without removing the sample from the transducer between the steps of exposing the sample to the transducer and irradiating the sample.

15. A method as claimed in claim 1, wherein the first and second reagents are the sole reagents present.

16. A device for detecting an analyte in a sample comprising:
a transducer having a pyroelectric or piezoelectric element and electrodes which is capable of transducing a change in energy to an electrical signal;
a first reagent immobilised on the transducer;
a second reagent releasably bound to the first reagent and having a label attached thereto which is capable of absorbing electromagnetic radiation to generate energy by non-radiative decay, wherein either the first or second reagent has a binding site which allows binding to the other and which is capable of preferentially binding to the analyte or a derivative of the analyte;
a source of electromagnetic radiation; and
a detector for detecting the electrical signal.

17. A device as claimed in claim 16, further comprising a sample chamber having two side walls, an upper surface and a lower surface, and wherein the transducer is located in the chamber.

18. A device as claimed in claim 16, wherein the transducer forms one of the side walls of the chamber.

19. A device as claimed in claim 16, wherein the transducer forms the upper surface of the chamber and the second reagent is more dense than the medium of the sample.

20. A device as claimed in claim 16, wherein the transducer forms the lower surface of the chamber and the second reagent is less dense than the medium of the sample.

21. A device as claimed in claim 16, wherein the first reagent is an immobilised antibody and the second reagent is a labelled analyte.

22. A method as claimed in claim 16, wherein the first reagent is an immobilised analyte and the second reagent is a labelled antibody.

23. A device as claimed in claim 16, further comprising a preservative coating over the transducer, first reagent and second reagent.

24. A device as claimed in claim 16, wherein the label is selected from a carbon particle, a coloured-polymer particle, a dye molecule, an enzyme, a fluorescent molecule, a metal, e.g. gold, particle, a haemoglobin molecule, a magnetic particle, a nanoparticle having a non-conducting core material and at least one metal shell layer, a red blood cell, and combinations thereof.

25. A device as claimed in claim 16, wherein the first reagent is adsorbed on to the transducer.

26. A device as claimed in claim 16, wherein the radiation source is adapted to generate a series of pulses of electromagnetic radiation and the detector is adapted to determine the time delay between each pulse of electromagnetic radiation from the radiation source and the generation of the electrical signal.

27. A device as claimed in claim 16, wherein the first and second reagents are the sole reagents in the device.

* * * * *